(12) United States Patent
Atil

(10) Patent No.: US 7,666,172 B2
(45) Date of Patent: Feb. 23, 2010

(54) MEDICAL NEEDLE HAVING A CLOSED TIP

(76) Inventor: Plaridel Cerna Atil, 130 W. Alosta Ave., Suite 314, Glendora, CA (US) 91740-1433

( * ) Notice: Subject to any disclaimer, the term of this patent is extended or adjusted under 35 U.S.C. 154(b) by 618 days.

(21) Appl. No.: 11/081,767

(22) Filed: Mar. 15, 2005

(65) Prior Publication Data
US 2006/0212004 A1    Sep. 21, 2006

(51) Int. Cl.
*A61M 5/32* (2006.01)
(52) U.S. Cl. ...................................... 604/272
(58) Field of Classification Search ............... 604/272, 604/274, 44, 46, 115, 239, 264, 273, 542; 606/167, 185
See application file for complete search history.

(56) References Cited

U.S. PATENT DOCUMENTS

| | | | | |
|---|---|---|---|---|
| 1,083,940 A * | 1/1914 | Pauls | ........................... | 604/272 |
| 2,634,726 A | 4/1953 | Hanson | | |
| 3,831,814 A * | 8/1974 | Butler | ........................... | 222/81 |
| 4,143,658 A * | 3/1979 | Rambosek et al. | ...... | 128/203.15 |
| 4,411,657 A * | 10/1983 | Galindo | ........................ | 604/274 |
| 4,413,993 A * | 11/1983 | Guttman | ..................... | 604/274 |
| 4,699,612 A * | 10/1987 | Hamacher | ................... | 604/506 |
| 4,838,877 A | 6/1989 | Massau | | |
| 5,254,106 A | 10/1993 | Feaster | | |
| 5,370,631 A | 12/1994 | Zhong | | |
| 5,487,725 A * | 1/1996 | Peyman | ....................... | 604/22 |
| 5,573,519 A | 11/1996 | Zohmann | | |
| 5,709,668 A | 1/1998 | Wacks | | |
| 5,848,996 A | 12/1998 | Eldor | | |
| 5,871,470 A | 2/1999 | McWha | | |
| 6,346,095 B1 | 2/2002 | Gross et al. | | |
| 6,517,521 B1 * | 2/2003 | Ly | .............................. | 604/239 |
| 6,558,353 B2 | 5/2003 | Zohmann | | |
| 6,613,026 B1 | 9/2003 | Palasis et al. | | |

* cited by examiner

*Primary Examiner*—Nicholas D Lucchesi
*Assistant Examiner*—Aarti B Berdichevsky
(74) *Attorney, Agent, or Firm*—Sheppard Mullin Richter & Hampton LLP (57) ABSTRACT

A needle is provided, having a closed tip configured to minimize tissue damage from penetration of the needle. The needle includes a tubular side wall defining an internal bore. The needle further includes an end wall angled relative to the needle's longitudinal axis and disposed at the distal end of the needle. The needle defines a distal opening spaced from the closed tip, providing access to the internal bore to facilitate fluid transfer. Preferably, the needle is configured to create a crescent-shaped penetration mark. The number and positioning of openings can be varied across embodiments of the invention, while maintaining a closed tip. For example, in certain embodiments, the needle comprises two distal openings defined by the side wall. A distal opening can also be provided by the end wall singly or in combination with additional distal openings.

25 Claims, 8 Drawing Sheets

MEDICAL NEEDLE HAVING A CLOSED TIP

BACKGROUND OF THE INVENTION

This invention relates generally to medical needles for delivery and extraction of fluid and, more particularly, to such medical needles having a closed tip.

Needles for delivery to, and extraction of fluid, from a body commonly have a hollow shaft that terminates in a pointed open end. Such needles are typically sized to suit particular applications. In dialysis treatments, blood is drawn from the patient, processed through a dialysis machine, and then the processed blood is injected back into the patient. Typically, an arteriovenus shunt, connecting an artery and a vein, is placed in the body, to provide spaced locations to facilitate blood transfer. Two opened-ended needles are used, a first needle to withdraw blood from the shunt, and a second needle to deliver the processed blood back into the shunt. Since the blood is transferred under pressure, these needles must be adequately sized to handle the flow of blood required. As a result, needles currently used in dialysis treatment commonly have a large opening at the distal end of the needle to accommodate the blood flow.

Although such open-end needles are generally effective for fluid transfer, shortfalls exist. For example, such needles can remove tissue when used (i.e., coring tissue), which, in dialysis treatment, can create problems with clotting and can inhibit the life of the shunt. Also, during treatment, cored tissue can hinder the flow of blood through the needle. Moreover, at the point of insertion, current needles commonly create circular penetration marks on the patient, which can impede healing. These shortfalls are not limited to needles used in dialysis treatment, but can also found in various other medical needles used for fluid delivery and extraction.

It should, therefore, be appreciated that there exists a need for a needle configured to facilitate fluid flow while minimizing tissue damage from penetration. The present invention fulfills this need and others.

SUMMARY OF THE INVENTION

Briefly, and in general terms, the invention provides a needle having a closed tip configured to minimize tissue damage from penetration of the needle. The needle includes a tubular side wall defining an internal bore. The needle further defines a distal opening spaced from the closed tip that provides access to the internal bore to facilitate fluid transfer. Disposed at the distal end of the needle, the needle further includes an end wall angled relative to the needle's longitudinal axis. In use, the needle provides smooth penetration, while the resulting penetration mark is comparatively small relative to the diameter of the needle, decreasing amount of debris that would otherwise enter the blood stream. Moreover, when used in dialysis treatment, the needle minimizes damage to the shunt, promoting an extended useable life for the shunt.

In a detailed aspect of an exemplary embodiment, an interface of the side wall and the end wall defines a rim circumscribing the end wall. The closed tip includes a distal most portion of the interface such that the closed tip is offset from the longitudinal axis.

In another detailed aspect of an exemplary embodiment, the closed tip has a rounded top profile and an acutely angled side profile. The end wall is angled between about 10 degrees and 30 degrees relative to the longitudinal axis of the needle body. Preferably, the needle is configured to create a crescent-shaped penetration mark.

The number and positioning of openings can be varied across embodiments of the invention, while maintaining a closed tip. For example, in certain embodiments, the needle comprises two distal openings defined by the side wall. A distal opening can also be provided by the end wall, singly or in combination with additional distal openings. In selected embodiments, the cumulative area of the cross-sections of the opening (or openings) substantially equals the cross-section of the internal bore.

In an exemplary embodiment of the invention, the concave end wall has a variable concavity profile, as viewed in sequential cross sections taken normal to the longitudinal axis. The closed tip is defined by a region that includes a distal most interface of the end wall and the tubular side wall such that the closed tip is offset from the longitudinal axis. The closed tip has a rounded top profile and an acutely angled side profile. In other embodiments, the tip can be pointed.

In an exemplary method of dialysis in accordance with the invention, blood is drawn from the patient, the blood is processed through a dialysis machine, and then the processed blood is injected back into the patient. In the exemplary embodiment, an arteriovenus shunt, connecting an artery and a vein, provides spaced locations to facilitate blood transfer. Two needles having a closed tip, e.g., such as the embodiments described above, are used. A first needle is used to withdraw blood from the shunt, and a second needle is used to deliver the processed blood back into the shunt. In use, the needles minimize damage to the shunt, promoting an extended useable life for the shunt. The needles decrease the amount of debris that would otherwise enter the blood stream. It is expected that the use of such needles will result in a reduction in the incidence of pulmonary hypertension currently seen in patients of chronic hemodialysis treatments.

For purposes of summarizing the invention and the advantages achieved over the prior art, certain advantages of the invention have been described herein. Of course, it is to be understood that not necessarily all such advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other advantages as may be taught or suggested herein.

All of these embodiments are intended to be within the scope of the invention herein disclosed. These and other embodiments of the present invention will become readily apparent to those skilled in the art from the following detailed description of the preferred embodiments having reference to the attached figures, the invention not being limited to any particular preferred embodiment disclosed.

BRIEF DESCRIPTION OF THE DRAWINGS

Embodiments of the present invention will now be described, by way of example only, with reference to the following drawings in which.

DETAILED DESCRIPTION OF THE PREFERRED EMBODIMENTS

Figure 1:
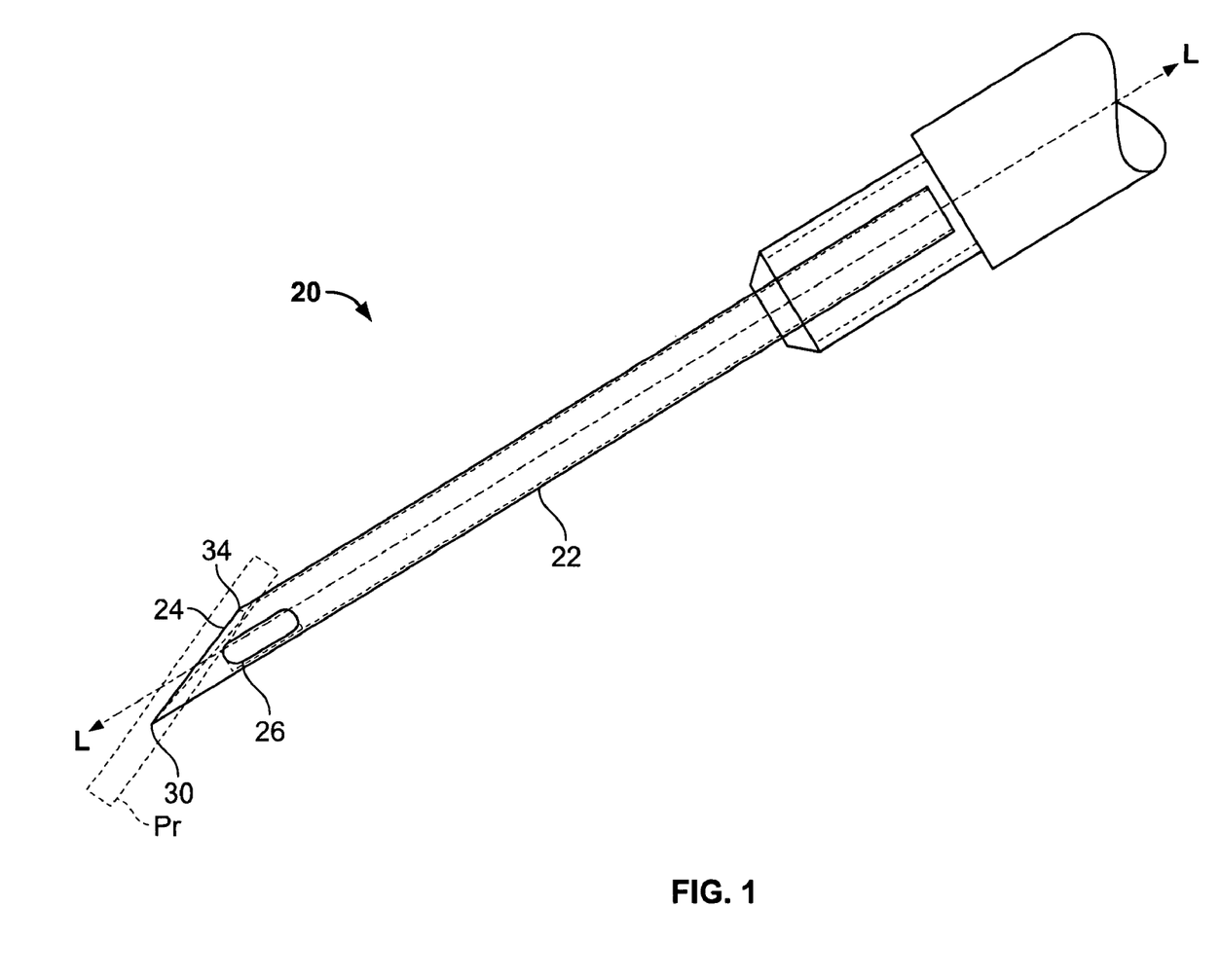
FIG. 1 is a side elevational view of a needle in accordance with the invention, the needle having a closed tip and two openings spaced from the tip.
Figure 3:
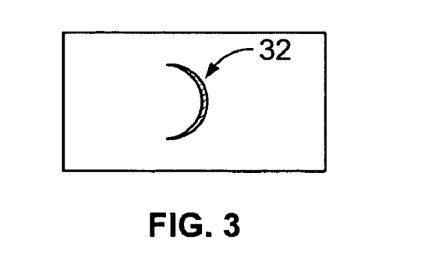
FIG. 3 shows a representative depiction of a penetration mark formed by the needle of FIG. 1.
Figure 4:
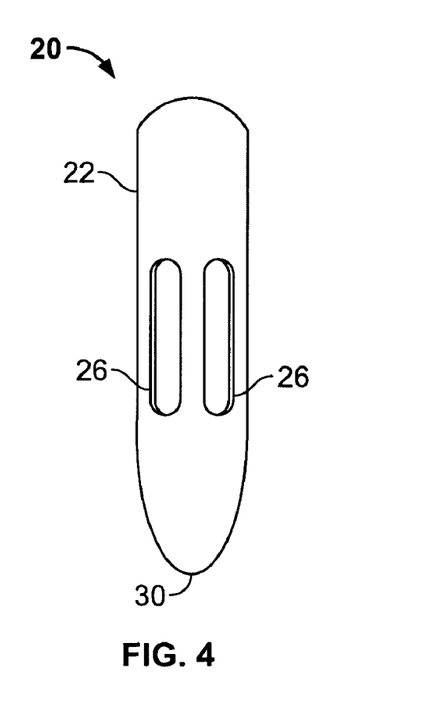
FIG. 4 is a top plan view of the needle of FIG. 1.
Figures 5, 6:
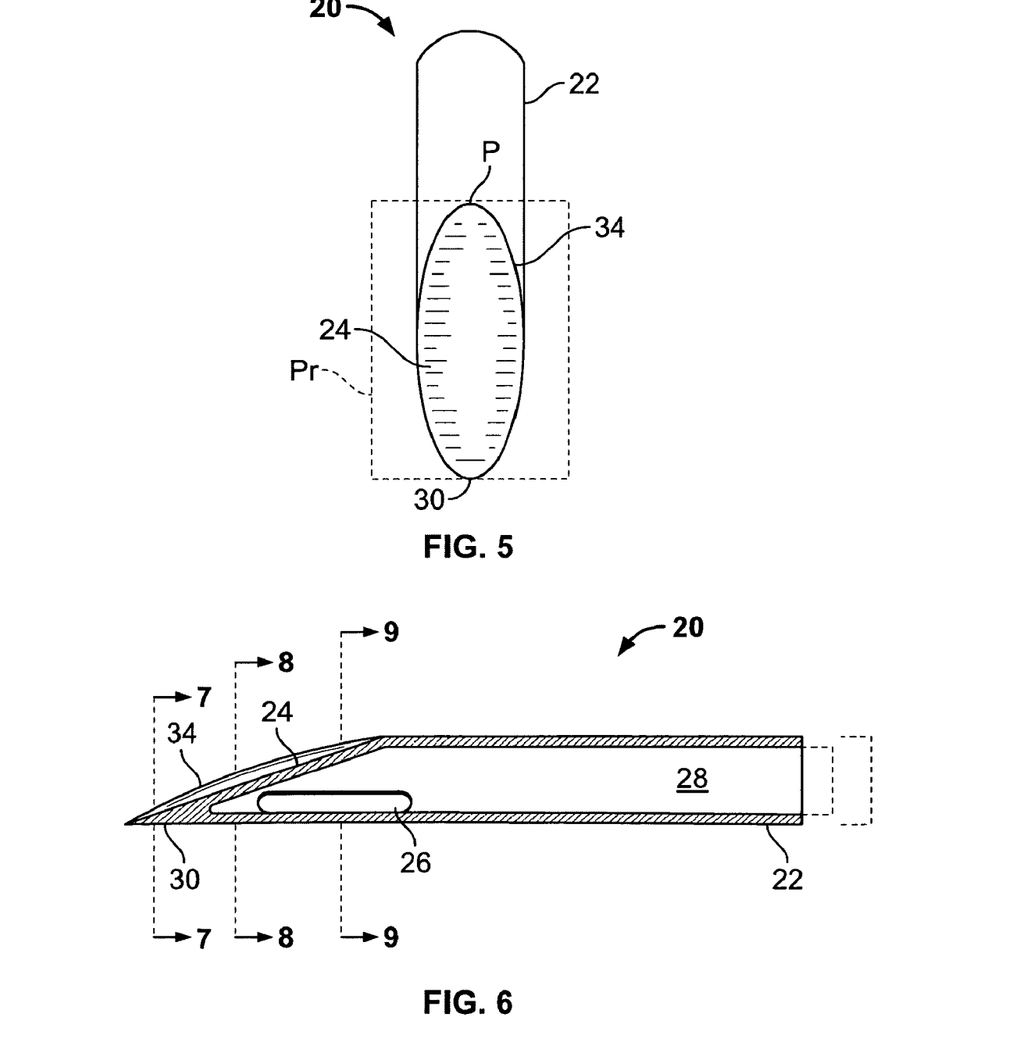
FIG. 5 is a back plan view of the needle of FIG. 1.
FIG. 6 is a longitudinal, cross-sectional view of the needle of FIG. 1.

With reference now to the drawings, and particularly FIG. 1, there is shown a needle 20 having a tubular side wall 22 and a concave end wall 24 slanted relative to a longitudinal axis (L) defined by the side wall. The side wall defines two openings 26 opposing the end wall that provide access to an internal bore 28 (FIG. 6). The needle terminates in a closed tip 30 designed to minimize coring, reducing debris passed into the blood stream, and otherwise inhibit damage from penetration. In use, the needle forms a penetration mark 32 having a crescent-shape (FIG. 3). When used in dialysis treatment, the needle minimizes damage to the shunt, promoting an extended useable life for the shunt. Moreover, the needle decreases debris that would otherwise enter the blood stream.

Figure 2:
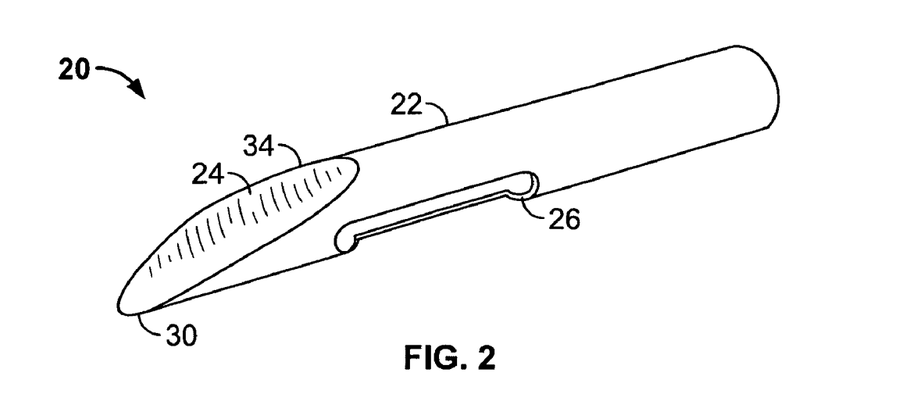
FIG. 2 is an isometric view of the needle of FIG. 1, depicting a concave end wall of the needle.

With reference now to FIG. 2, the side wall 22 and the end wall 24 interface at a rim 34 circumscribing the end wall. The closed tip 30 is offset from the longitudinal axis (L), and it includes a distal most portion of the rim. As best seen in FIG. 5, the tip has a rounded profile, as view from above, while having a thin side profile (see, FIG. 7). In use, the needle provides smooth penetration, while the resulting penetration mark 32 is comparatively small relative to the diameter of the needle. In the exemplary embodiment, the needle has an outer diameter of about 1.8 mm. For convenience of reference, in this embodiment, the rim can be considered as generally residing on a plane that can serve as a reference plane ($P_r$) for the end wall. As seen in FIG. 6, the reference plane ($P_r$) is angled about 17 degrees relative to the longitudinal axis of the needle body. In other selected embodiments, the angle of the end wall can vary, e.g., between about 10 degrees and 30 degrees relative to the longitudinal axis of the needle body and, more preferably, between about 19 degrees and 29 degrees.

The openings 26 are spaced from the tip 30 and are sized to facilitate smooth flow of fluid through the needle, during dialysis treatment. The internal bore 28 (FIG. 6) has a diameter of about 1.6 mm. Each opening has a length of about 3 mm and a width of about 0.8 mm. In other embodiments, the size of the openings and the internal bore can be set to accommodate particular requirements for the intended use, to include volume, pressure requirements. The number and positioning of openings can also be varied. In selected embodiments, the cumulative area of the cross-sections of the opening (or openings) substantially equals the cross-section of the internal bore.

Figure 7:
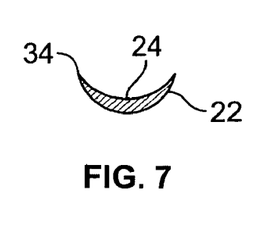
FIG. 7 is a cross-sectional view, taken along line 8-8 of FIG. 6, of the needle of FIG. 1.
Figure 8:
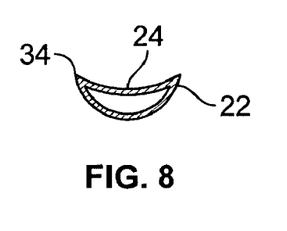
FIG. 8 is a cross-sectional view, taken along line 9-9 of FIG. 6, of the needle of FIG. 1.
Figure 9:
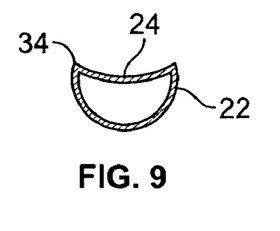
FIG. 9 is a cross-sectional view, taken along line 10-10 of FIG. 6, of the needle of FIG. 1.
Figure 10:
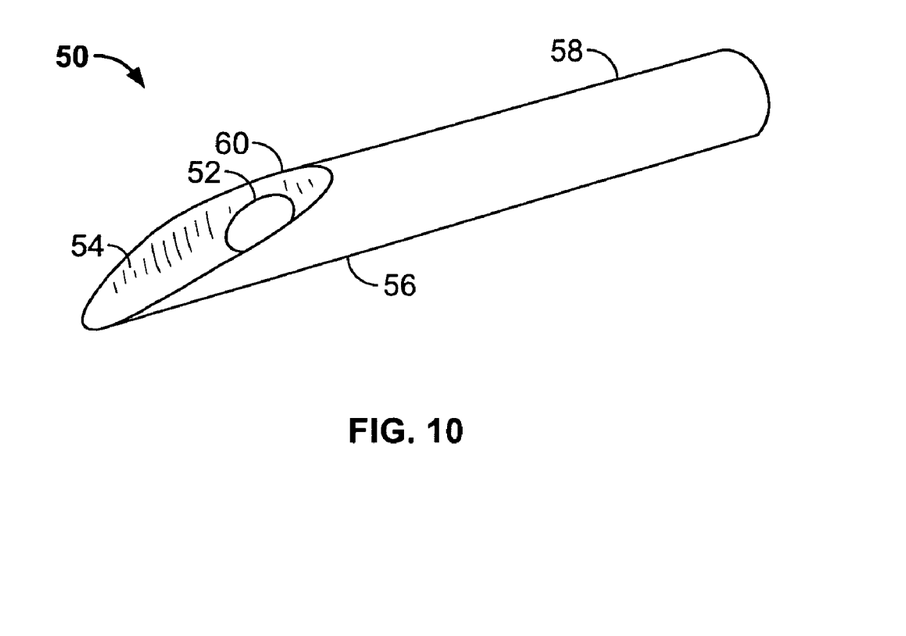
FIG. 10 is an isometric view, similar to FIG. 2, of a second embodiment of a needle in accordance with the invention.
Figure 11:
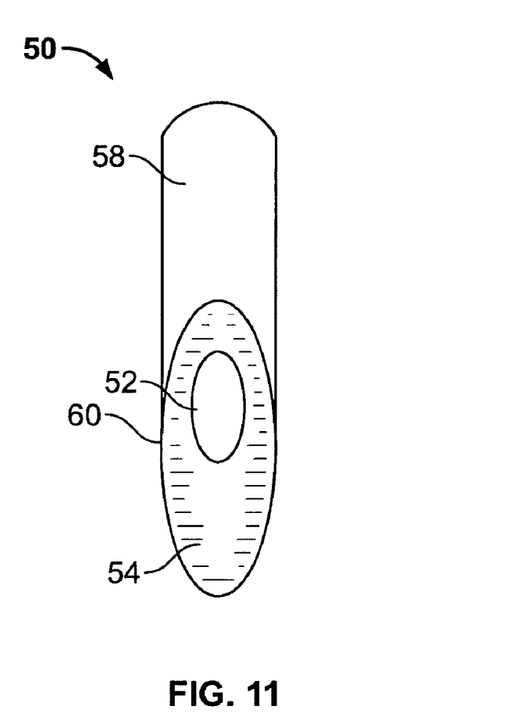
FIG. 11 is a top plan view of the needle of FIG. 10.
Figure 12:
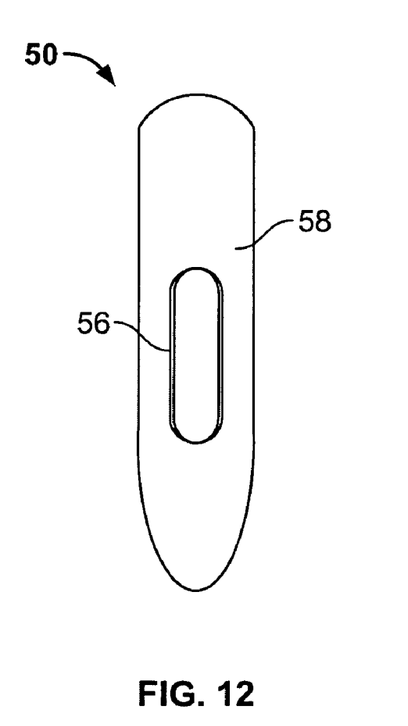
FIG. 12 is a back plan view of the needle of FIG. 10.

In FIGS. 6-8, the needle 20 is viewed in spaced cross-sections about the end wall 24, taken normal to the longitudinal axis (L). In the exemplary embodiment, the concavity of the end wall decreases as the end wall extends rearward. In proximity to the tip 30, the end wall 24 is comparatively more concave than it is in proximity to its proximal point (P) (FIG. 5). In turn, the concavity of the end wall is comparatively shallower in proximity to point (P). As a result, in proximity to the closed tip, the rim 34 is defined by an acute angle between the end wall and the side wall, providing a sharp edge that aids in smooth penetration. As best seen in FIG. 6, the rim is generally arced as it extends about the side wall from the tip from the tip rearward. In the exemplary embodiment, as viewed from the longitudinal cross-section (FIG. 6), the rim has a radius of curvature of about 12 mm.

Figure 13:
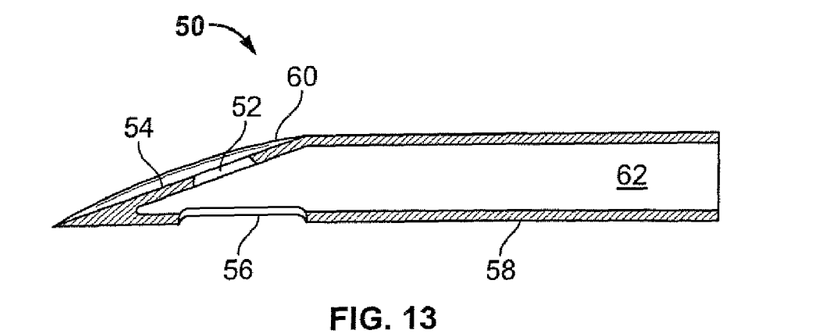
FIG. 13 is a longitudinal, cross-sectional view of the needle of FIG. 10.
Figure 14:
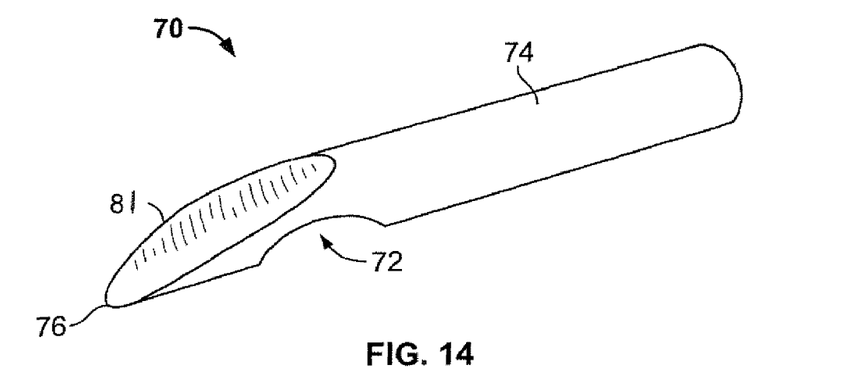
FIG. 14 is an isometric view, similar to FIG. 2, of a third embodiment of a needle in accordance with the invention.
Figure 15:
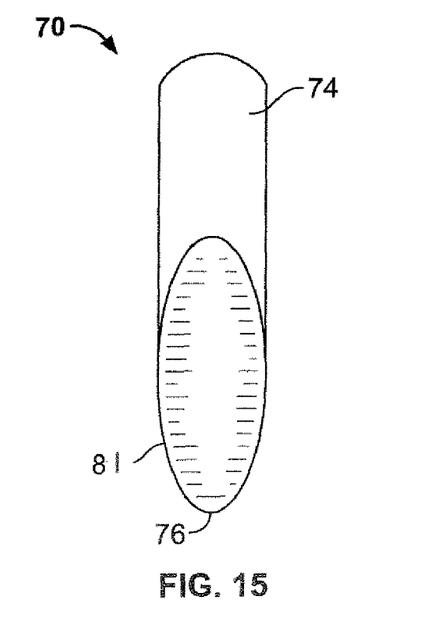
FIG. 15 is a top plan view of the needle of FIG. 14.
Figure 16:
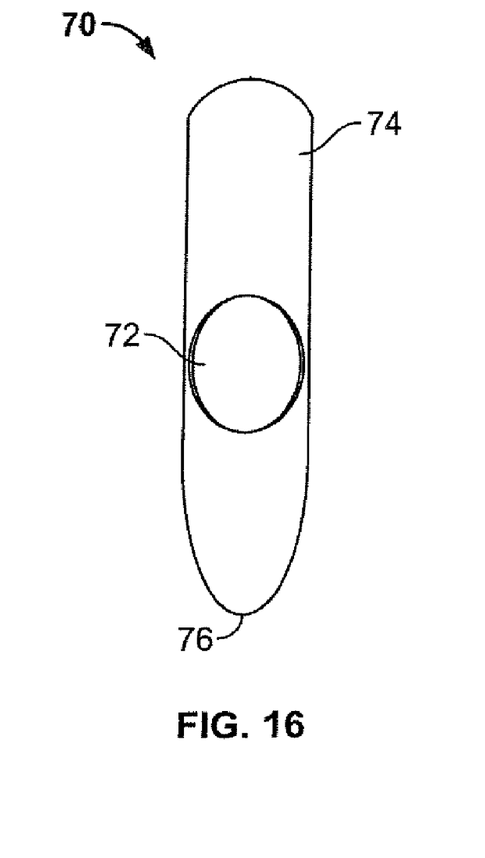
FIG. 16 is a back plan view of the needle of FIG. 14.
Figure 17:
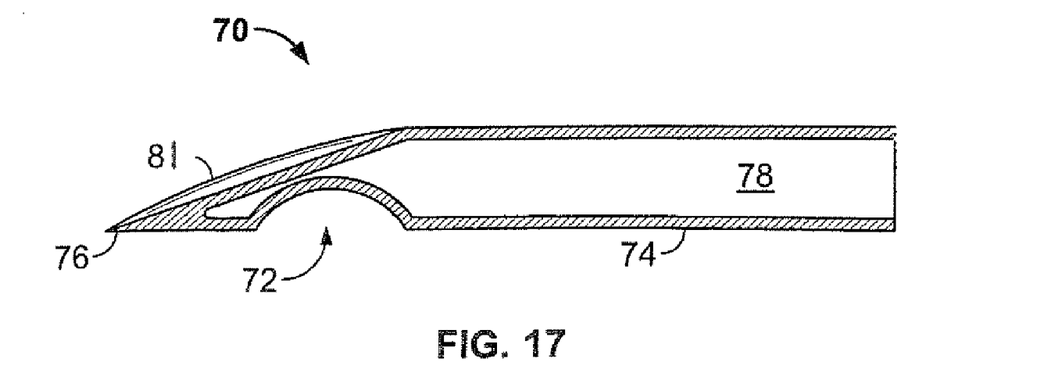
FIG. 17 is a longitudinal, cross-sectional view of the needle of FIG. 14.

With reference now to FIGS. 10-13, a second embodiment of a needle 50 is shown. The needle 50 is similar to the needle 20 of FIG. 1, though the configurations of the openings differ. In this embodiment, a first opening 52 defined by the end wall 54 and a second opening 56 defined by the side wall 58. The first opening is positioned near proximal point (P) of the end wall. The rim 60 of the needle is raised relative the first opening, as viewed from the side (FIG. 13). The second opening is approximately 180 degrees about the needle relative to the first opening. The openings are sized to facilitate flow through the internal bore 62 of the needle and are sufficiently positioned to inhibit coring of tissue.

With reference now to FIGS. 14-17, a third embodiment of a needle 70 is shown. In this embodiment, the needle provides a single opening 72 defined by the side wall 74, proximate to the closed tip 76. The opening is approximately 180 degrees about the needle relative to the end wall 81. The area of the opening substantially equals the cross-sectional area of the internal bore 78. In use, the needle preferably is inserted at an angle with the opening facing downward.

Figure 18:
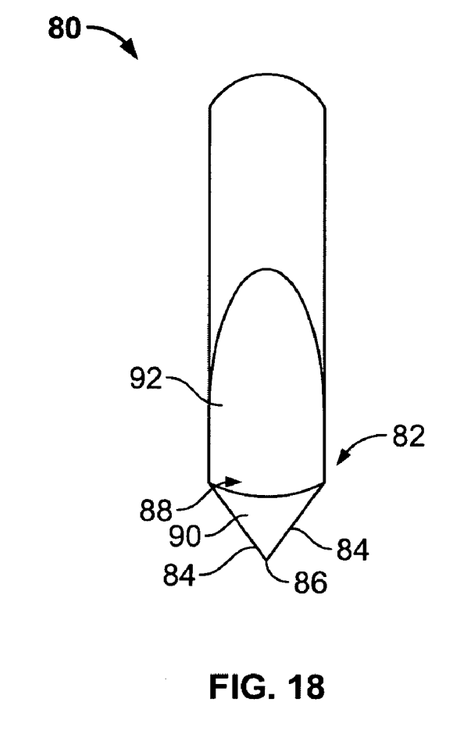
FIG. 18 is a top plan view of a fourth embodiment of a needle in accordance with the invention.
Figure 19:
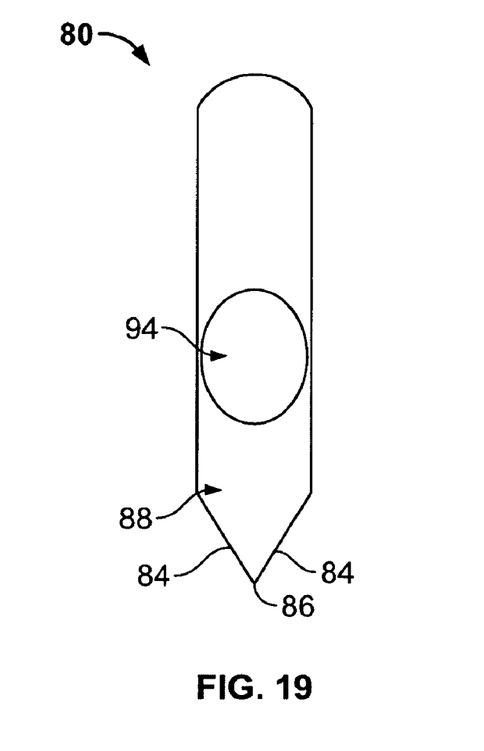
FIG. 19 is a back plan view of the needle of FIG. 18.

With reference now to FIGS. 18 and 19, a fourth embodiment of a needle 80 is provided. In this embodiment, the needle defines in a closed tip 82 having two side edges 84 that terminate in a point 86. An end wall 88 of the needle includes a flat portion 90 proximate to the point and a concave portion 92. The needle further defines an opening 94 spaced from the closed tip.

Figure 20:
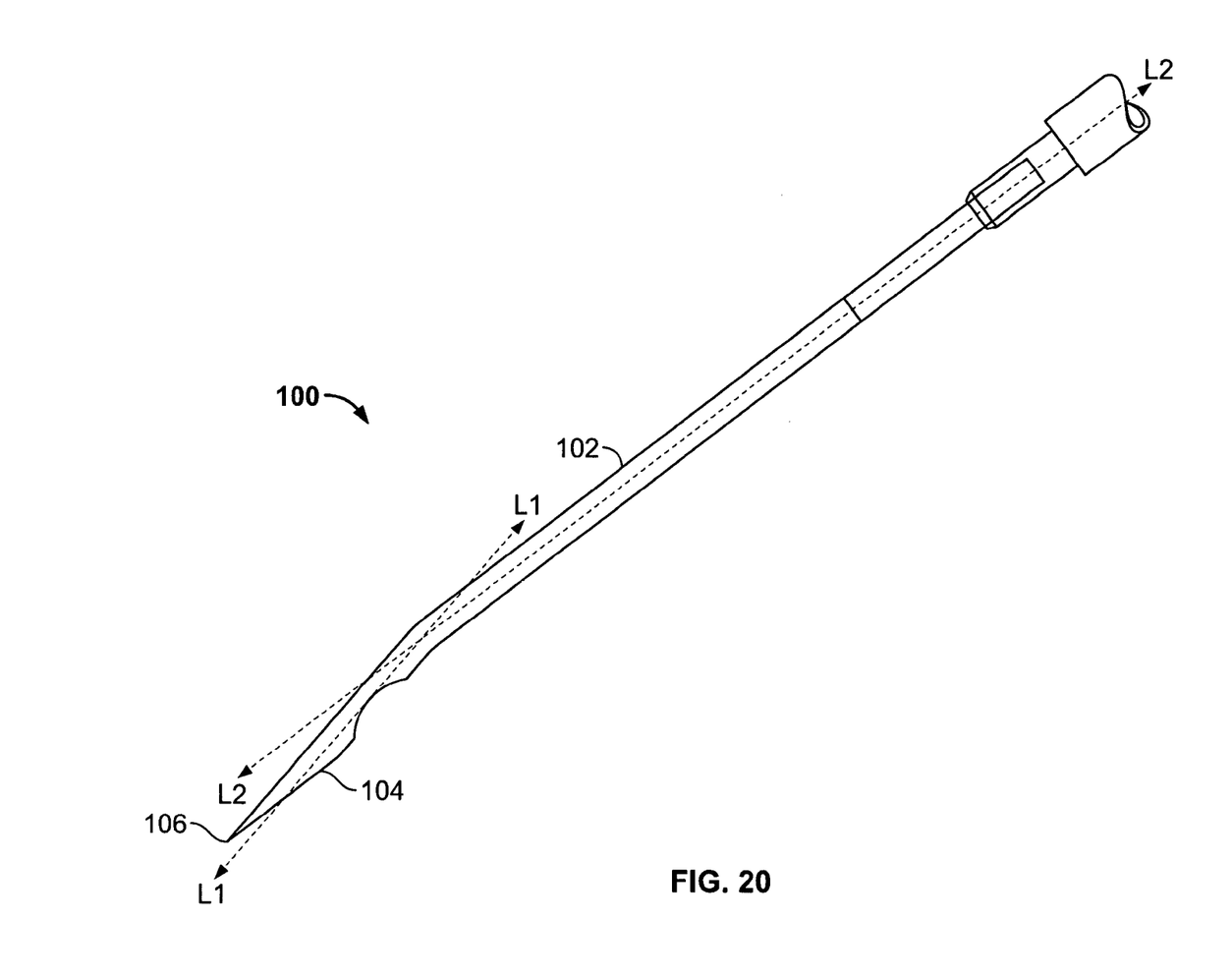
FIG. 20 is a side elevational view of a fifth embodiment of a needle in accordance with the invention.
Figure 21:
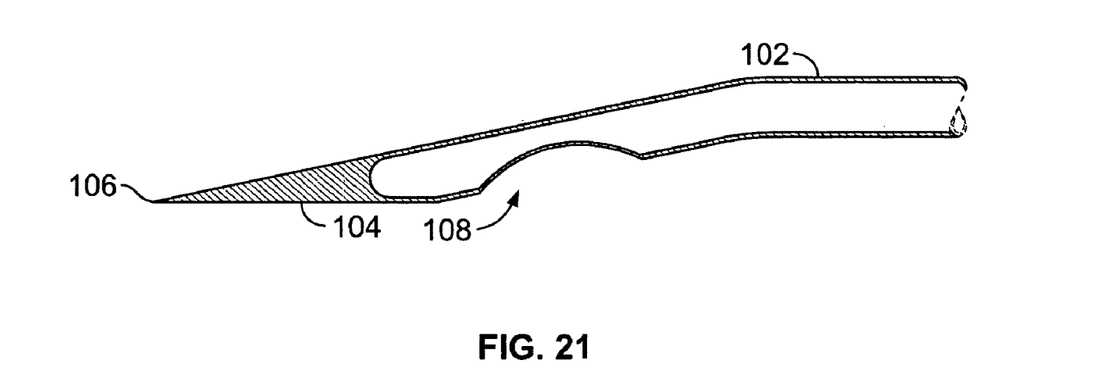
FIG. 21 is a side cross-sectional view of the needle of FIG. 20.

A fifth embodiment, needle 100, is depicted in FIGS. 20 and 21. The needle includes a side wall 102 and an end wall 104. In this embodiment, the side wall includes a bend, thereby defining two longitudinal axes (L1, L2) that are angled relative to each other. The end wall is generally flat and terminates in a point 106. An opening 108 is defined by the side wall providing access to a bore of the needle.

In an exemplary method of dialysis in accordance with the invention, blood is drawn from the patient, processed through a dialysis machine, and then the processed blood is injected back into the patient. In the exemplary embodiment, an arteriovenus shunt, connecting an artery and a vein, provides spaced locations to facilitate blood transfer. Two needles having a closed tip, e.g., such as the embodiments described above. A first needle is used to withdraw blood from the shunt, and a second needle to deliver the processed blood back into the shunt. In use, the needles minimize minimizes damage to the shunt, promoting an extended useable life for the shunt. The needles decreases amount of debris that would otherwise enter the blood stream. It is expected that the use of such needles will result in a reduction in the incidence of pulmonary hypertension currently seen in patents of chronic hemodialysis treatments.

It should be appreciated from the foregoing that the invention provides a needle having a closed tip and configured to minimize tissue damage from penetration of the needle. The needle includes a tubular side wall defining an internal bore. The needle further includes an end wall angled relative to the needle's longitudinal axis and disposed at the distal end of the needle. The needle defines a distal opening spaced from the closed tip, providing access to the internal bore to facilitate fluid transfer. Preferably, the needle is configured to create a crescent-shaped penetration mark. The number and positioning of openings can be varied across embodiments of the invention, while maintaining a closed tip. For example, in certain embodiments, the needle comprises two distal openings defined by the side wall. A distal opening can also be provided by the end wall singly or in combination with additional distal openings.

Although the invention has been disclosed in detail with reference only to the exemplary embodiments, those skilled in the art will appreciate that various other embodiments can be provided without departing from the scope of the invention. Accordingly, the invention is defined only by the claims set forth below.

I claim:

1. A needle, comprising
   a tubular side wall defining an internal bore, the tubular side wall further defining a longitudinal axis;
   a concave end wall disposed at a distal end of the side wall, the end wall angled relative to the longitudinal axis;
   a closed tip defined by a region that includes a distal-most interface of the end wall and the tubular side wall; and
   a proximal point defined by a region that includes a proximal-most interface of the end wall and the tubular side wall;
   wherein a distal opening is defined spaced from the closed tip and provides access to the internal bore;
   wherein the end wall has a variable concavity profile, as viewed in sequential cross sections taken normal to the longitudinal axis; and
   wherein the concavity of the end wall decreases as the end wall extends away from the closed tip, as viewed in sequential cross sections taken normal to the longitudinal axis, so that the end wall is comparatively more concave in proximity to the closed tip than it is in proximity to the proximal point.

2. A needle as defined in claim 1, wherein the closed tip has a rounded top profile and an acutely angled side profile.

3. A needle as defined in claim 1, wherein the end wall is angled between about 10 degrees and 30 degrees relative to the longitudinal axis.

4. A needle as defined in claim 1, wherein the needle is configured to create a crescent-shaped penetration mark.

5. A needle as defined in claim 1, wherein a cross section of the distal opening approximates a cross section of the internal bore.

6. A needle as defined in claim 1, wherein two distal openings are defined by the side wall.

7. A needle as defined in claim 1, wherein the closed tip is offset from the longitudinal axis.

8. A needle as defined in claim 7, wherein:
   the tubular side wall has a radius in a region proximate the distal opening; and
   the closed tip is offset from the longitudinal axis by a distance substantially equal to the radius of the tubular side wall in the region proximate the distal opening.

9. A needle as defined in claim 1, wherein an interface of the side wall and the end wall defines a rim circumscribing the end wall.

10. A needle as defined in claim 9, wherein:
    the end wall defines an end wall axis extending substantially orthogonally to the end wall; and
    the rim circumscribing the end wall is arced convexly relative to a plane extending orthogonally to the end wall axis.

11. A needle as defined in claim 1, wherein the distal opening is defined by the end wall.

12. A needle as defined in claim 11, wherein a second distal opening is defined by the side wall.

13. A needle, comprising
    a tubular side wall defining an internal bore, the tubular side wall further defining a longitudinal axis;
    a concave end wall disposed at a distal end of the side wall such that an interface of the side wall and the end wall defines a rim circumscribing the end wall, the end wall angled relative to the longitudinal axis; and
    a closed tip at the distal end, the closed tip including a distal-most portion of the interface of the end wall and the tubular side wall such that the closed tip is offset from the longitudinal axis;
    wherein a distal opening is defined spaced from the closed tip and provides access to the internal bore;
    wherein the end wall defines an end wall axis extending substantially orthogonally to the end wall; and
    wherein the rim circumscribing the end wall is arced convexly relative to a plane extending orthogonally to the end wall axis.

14. A needle as defined in claim 13, wherein the closed tip has a rounded top profile and an angled side profile.

15. A needle as defined in claim 13, wherein the needle is configured to create a crescent-shaped penetration mark.

16. A needle as defined in claim 13, wherein two distal openings are defined by the side wall.

17. A needle as defined in claim 13, further comprising a proximal point defined by a region that includes a proximal-most interface of the end wall and the tubular side wall;
    wherein the end wall has a variable concavity profile, as viewed in sequential cross sections taken normal to the longitudinal axis; and
    wherein the concavity of the end wall decreases as the end wall extends away from the closed tip, as viewed in sequential cross sections taken normal to the longitudinal axis, so that the end wall is comparatively more concave in proximity to the closed tip than it is in proximity to the proximal point.

18. A needle as defined in claim 13, wherein:
    the tubular side wall has a radius in a region proximate the distal opening; and
    the closed tip is offset from the longitudinal axis by a distance substantially equal to the radius of the tubular side wall in the region proximate the distal opening.

19. A needle as defined in claim 13, wherein the distal opening is defined by the end wall.

20. A needle as defined in claim 19, wherein a second distal opening is defined by the side wall.

21. A needle, comprising
    a tubular side wall defining an internal bore, the tubular side wall further defining a longitudinal axis;
    a concave end wall disposed at a distal end of the side wall, the end wall angled relative to the longitudinal axis, the end wall having a variable concavity profile, as viewed in sequential cross sections taken normal to the longitudinal axis;

a closed tip defined by a region that includes a distal-most interface of the end wall and the tubular side wall such that the closed tip is offset from the longitudinal axis, the closed tip having a rounded top profile and an acutely angled side profile; and a proximal point defined by a region that includes a proximal-most interface of the end wall and the tubular side wall;

wherein a distal opening is defined by the side wall, spaced from the closed tip and in proximity to the end wall, providing access to the internal bore;

wherein the concavity of the end wall decreases as the end wall extends away from the closed tip, as viewed in sequential cross sections taken normal to the longitudinal axis, so that the end wall is comparatively more concave in proximity to the closed tip than it is in proximity to the proximal point.

22. A needle as defined in claim 21, wherein a second distal opening is defined by the side wall.

23. A needle as defined in claim 21, wherein a second distal opening is defined by the end wall.

24. A needle as defined in claim 21, wherein:
the tubular side wall has a radius in a region proximate the distal opening; and
the closed tip is offset from the longitudinal axis by a distance substantially equal to the radius of the tubular side wall in the region proximate the distal opening.

25. A needle as defined in claim 21, wherein:
an interface of the side wall and the end wall defines a rim circumscribing the end wall;
the end wall defines an end wall axis extending substantially orthogonally to the end wall; and
the rim circumscribing the end wall is arced convexly relative to a plane extending orthogonally to the end wall axis.

* * * * *

UNITED STATES PATENT AND TRADEMARK OFFICE
CERTIFICATE OF CORRECTION

| | | |
|---|---|---|
| PATENT NO. | : 7,666,172 B2 | Page 1 of 1 |
| APPLICATION NO. | : 11/081767 | |
| DATED | : February 23, 2010 | |
| INVENTOR(S) | : Atil | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1025 days.

Signed and Sealed this
Twenty-fourth Day of May, 2011

David J. Kappos
*Director of the United States Patent and Trademark Office*